(12) United States Patent
Buvat et al.

(10) Patent No.: US 8,993,700 B2
(45) Date of Patent: Mar. 31, 2015

(54) FLUORESCENT POLYMERS OF 7-HYDROXYCOUMARIN COMPOUNDS, CHEMICAL SENSORS COMPRISING THEM, AND POLYMERIZABLE FLUORESCENT COMPOUND OF 7-HYDROXYCOUMARIN

(75) Inventors: Pierrick Buvat, Montbazon (FR); Lucie Malosse, Clermont-Ferrand (FR); Alain Siove, Soisy-Sous-Montmorency (FR); Dominique Ades, Cormeilles-en-Parisis (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 13/498,090

(22) PCT Filed: Sep. 24, 2010

(86) PCT No.: PCT/EP2010/064181
§ 371 (c)(1),
(2), (4) Date: Mar. 28, 2012

(87) PCT Pub. No.: WO2011/036269
PCT Pub. Date: Mar. 31, 2011

(65) Prior Publication Data
US 2012/0178172 A1 Jul. 12, 2012

(30) Foreign Application Priority Data

Sep. 25, 2009 (FR) ...................................... 09 56656

(51) Int. Cl.
*C08F 24/00* (2006.01)
*C07D 311/00* (2006.01)
*C09B 69/10* (2006.01)
*C09B 57/02* (2006.01)
*G01N 33/52* (2006.01)

(52) U.S. Cl.
CPC .............. *C09B 69/109* (2013.01); *C09B 57/02* (2013.01); *G01N 33/52* (2013.01)
USPC .......................................... 526/266; 549/289

(58) Field of Classification Search
USPC .......................................... 549/289; 526/266
See application file for complete search history.

(56) References Cited

U.S. PATENT DOCUMENTS

| | | | | |
|---|---|---|---|---|
| 5,019,350 A * | 5/1991 | Rhum et al. | ............... | 422/82.07 |
| 5,208,350 A | 5/1993 | Bouma et al. | | |
| 5,858,652 A | 1/1999 | Laffler et al. | | |
| 8,133,411 B2 | 3/2012 | Charreyre et al. | | |
| 8,178,354 B2 | 5/2012 | Hairault et al. | | |
| 2007/0254859 A1 | 11/2007 | Wempe et al. | | |

FOREIGN PATENT DOCUMENTS

| | | |
|---|---|---|
| EP | 0357011 A2 | 3/1990 |
| FR | 2887892 A1 | 1/2007 |
| FR | 2900408 A1 | 11/2007 |
| WO | 9631565 A1 | 10/1996 |
| WO | 2005103653 A1 | 11/2005 |

OTHER PUBLICATIONS

Krejcoves et al. Collection of Czechoslav.Chem.Commun. 1979, 44, 2211-2213.*
Bardez et al. Chemical Physics Letters 1992, 191 (1,2), 142-148.*
Krejcoves, et al., "The Preparation and Characterization of Some Novel Flourescence Labels Derived from 7-Substituted 2H-1-Benzopyrane-2-Ones", Collection of Czechoslovak Chemical Communications, Institute of Organic Chemistry & Biochemistry, Prague; CZ, vol. 44, Jan. 1, 1979 pp. 2211-2220.
International Search Report and Written Opinion issued on Dec. 1, 2010 for International Application No. PCT/EP2010/064181.
International Patentability Preliminary Report issued on Jan. 17, 2012 for International Application No. PCT/EP2010/064181.
Demand filed on Feb. 21, 2011 in International Application No. PCT/EP2010/064181.
Monfort-Windels, "Lumiere et Matiere: Des Interactions au Service De La Lutte Contre La Contrefacon", L'actualite Chimique, 2007, No. 308-309, pp. 108-110.
Thery, "La Trace Mise En Lumiere Dans l'enquete Policiere", L'actualite Chimique, 2007, No. 308-309, pp. 111-112.
Jenkins et al., "Polymer-Based Lanthanide Luminescent Sensor for Detection of the Hydrolysis Product of the Nerve Agent Soman in Water", Analytical Chemistry, Jan. 15, 1999, vol. 71, No. 2, pp. 373-378.
Jenkins et al., "Molecularly imprinted polymer sensors for pesticide and insecticide detection in water", Analyst, 2001, vol. 126, pp. 798-802.
Campbell et al., "Fluorescent Hard-Sphere Polymer Colloids for Confocal Microscopy", Journal of Colloid and Interface Science, 2002, vol. 256, pp. 325-330.
Uchiyama et al.,"Fluorescent Molecular Thermometers Based onPolymers Showing Temperature-Induced Phase Transitions and Labeled with Polarity-Responsive Benzofurazans", Analytical Chemistry, 2003, vol. 75, pp. 5926-5935.
Trenor et al., "Coumarins in Polymers: From Light Harvesting to Photo-Cross-Linkable Tissue Scaffolds", Chemical Reviews, 2004, vol. 104, No. 6, pp. 3059-3077.
Bardez et al., "Photoinduced biprotonic transfer in 4-methylumbelliferone", Chemical Physics Letters, Mar. 27, 1992, vol. 191, No. 1,2 pp. 142-148.
Cohen et al., "Excited State Proton-Transfer Reactions of Coumarin 4 in Protic Solvents", J. Phys. Chem. A, 2001, vol. 105, pp. 7157-7164.
Schulman et al., "Tautomerization Kinetics of 7-Hydroxy-4-methylcoumarin in the Lowest Excited Singlet State", The Journal of Physical Chemistry, 1979, vol. 83, No. 4, pp. 447-451.
Abdel-Mottaled et al., "Fluorescence Properties and Excited State Interactions of 7-Hydroxy-4-Methylcoumarin Laser Dye", Journal of Photochemistry and Photobiology, A: Chemistry, 1989, vol. 46, pp. 379-390.

(Continued)

*Primary Examiner* — Nizal Chandrakumar
(74) *Attorney, Agent, or Firm* — Knobbe, Martens, Olson & Bear, LLP (57) ABSTRACT

Polymers and copolymers of polymerizable fluorescent compounds of 7-hydroxycoumarin such as Ethyl-2-methacrylate Umbelliferone-4-acetate are provided. In addition, a sensor comprising this polymer notably for detecting and/or assaying nitrated and organophosphorus compounds, explosives, and toxic compounds is provided.

19 Claims, 2 Drawing Sheets

(56) References Cited

OTHER PUBLICATIONS

Kudo et al., "Effect of a hyaluronan synthase suppressor, 4-methylumbelliferone, on B16F-10 melanoma cell adhesion and locomotion", Biochemical and Biophysical Research Communications, 2004, vol. 321, pp. 783-787.

Nakamura et al., "Suppression of matrix metalloproteinase-9 by 4-methylumbelliferone", 2007, Cell Biology International, vol. 31, pp. 1022-1026.

Yoshihara et al., "A hyaluronan synthase suppressor, 4-methylumbelliferone, inhibits liver metastasis of melanoma cells", FEBS Letters, 2005, vol. 579, pp. 2722-2726.

Donglei et al., "Recent Progress in the Developmentof Coumarin Derivatives as Potent Anti-HIVAgents", Medicinal Research Reviews, 2003, vol. 23, No. 3, pp. 322-345.

Pal et al., "Characterization of the Fluorophore 4-Heptadecyl-7-hydroxycoumarin: A Probe for the Head-Group Region of Lipid Bilayers and Biological Membranes", Biochemistry, 1985, vol. 24, pp. 573-581.

Microspheres and Qdot Nanocrystals for Tracing—Section 14,6, Life Technologies, pp. 1-10, Publication date: Unknown, Downloaded from "http://www.invitrogen.com/site/us/en/home/References/Molecular-Probes-The-Handbook/Fluorescent-Tracers-of-Cell-Morphology-and-Fluid-Flow/FluoSpheres-and-TransFluoSpheres-Microspheres-for-Tracing.html" on Sep. 13, 2012.

Chujo et al., "Polyoxazoline Having a Coumarin Moiety as a Pendant Group. Synthesis and Photogelation", Macromolecules, 1990, vol. 23, pp. 2693-2697.

Pitschke et al., "Polymeric fluorescent dyes for labeling of proteins and nucleic acids", Colloid & Polymer Science, 1995, vol. 273, No. 8, pp. 740-752.

Rathbone et al., "Molecular recognition by fluorescent imprinted polymers", Tetrahedron Letters, 2000, vol. 41, pp. 123-126.

Krasnaya, et al., "Reactions of animals of conjugated unsaturated omega-dimethylaminoaldehydes with coumarin derivatives", Izvestiya Akademii Nauk, Seriya Khimicheskaya, No. 3, 1995, pp. 537-543. English abstract is enclosed at p. 543.

French Search Report dated Jun. 1, 2010 of French Application No. 0956656—2 pages.

* cited by examiner

FLUORESCENT POLYMERS OF 7-HYDROXYCOUMARIN COMPOUNDS, CHEMICAL SENSORS COMPRISING THEM, AND POLYMERIZABLE FLUORESCENT COMPOUND OF 7-HYDROXYCOUMARIN

RELATED APPLICATIONS

This application is a U.S. National Phase of International Application No. PCT/EP2010/064181, filed Sep. 24, 2010, designating the U.S., and published in French as WO 2011/036269 on Mar. 31, 2011 which claims the benefit of French Patent Application No. 09 56656 filed Sep. 25, 2009.

TECHNICAL FIELD

The invention relates to fluorescent polymers obtainable by polymerization of fluorescent polymerizable compounds of 7-hydroxycoumarin and more particularly of Ethyl-2-methacrylate Umbelliferone-4-acetate.

More specifically, the invention relates to polymers of fluorescent, notably polar and hydrophobic derivatives of 7-hydroxycoumarin comprising in position 4, a polymerizable substituent which does not modify or which does not substantially modify the electronic properties and photoluminescence of the coumarin ring.

The invention also relates to a novel polymerizable fluorescent compound of 7-hydroxycoumarin and to its preparation.

The invention further relates to sensors comprising these fluorescent polymers as a sensitive material, notably for detecting and/or assaying nitrated or organophosphorus compounds, explosives and toxic compounds.

The invention finally relates to the use of these fluorescent polymers for making fluorescent probes, biological markers, and fluorescent, photoluminescent and/or radioluminescent and/or cathodoluminescent materials.

The technical field of the invention may thus generally be defined as that of fluorescent polymers.

BACKGROUND

Today, there is an increasing demand for fluorescent polymers in very diverse sectors. Thus, in the field of security, fluorescent marking is of interest for fighting against counterfeiting [1]. In the field of forensics, it is applied in police investigations [2]. Fluorescent polymers are also used in chemical sensors for detecting pollutants or toxic compounds in water or in air [3] [4] [5] and [6].

Fluorescent polymers may also find applications in the field of imaging, notably confocal microscopy [7] or fluorescence microscopy.

In the therapeutical or pharmaceutical fields, fluorescent polymers may be coupled with a biological ligand and thus used in tests for detecting target molecules [8].

In the field of graphic arts, they may be used in paints, inks for textile printing or for engraving [9].

Other original applications of fluorescent polymers are also listed in the literature, such as the one described by Uchiyama et al. [10] who have developed fluorescent molecular thermometers by coupling poly(N-isopropylacrylamide), known for undergoing a phase transition in an aqueous solution around 32° C., with a fluorescent derivative of the benzofurazane type, the fluorescence of which depends on the polarity of the solvent.

If the interest is now focused on coumarins, umbelliferone (or 7-hydroxycoumarin) has blue fluorescence emission (300, 305 and 325 nm) when it is excited by a radiation located in the ultraviolet range. A great number of its derivatives are of great importance in physics, chemistry, biology and medicine and have been used for various applications [11].

In particular, the photochemical and photophysical properties in the excited state of 4-methylumbelliferone (4MU) have been known for a long time and this fluorophore was used as a pH probe and as a laser dye [12] [13] and [14].

In the biomedical field, 4MU has also proved to be an inhibitor of the synthesis of hyaluronic acid [16] [17] [18], which is one of the main components of the extracellular matrix which significantly contributes to proliferation and migration of cells and which is thus involved in the progression of certain malignant tumors. A recent review by Yu et al. [19] moreover describes the study of more than 150 derivatives of the coumarin type and their efficiency as anti-HIV agents. Lipophilic 4-heptadecyl-7-hydroxycoumarin, as for it, has been used as a probe for studying properties of phospholipid bilayers at the water/lipid interface or for measuring pH differences at membrane interfaces [20].

Easy to couple with other entities through conventional chemistry, coumarins are attractive because of their original properties, i.e. notably absorption and emission of light which may be modulated, and reversible photodimerization. The idea of using them in polymers for synthesizing macromolecular architectures with specific properties, therefore appeared rapidly [11].

For example, the photodimerization and photocleavage properties of coumarins have been utilized for making liquid crystal polymers and biodegradable polypeptides. Other uses have the purpose of obtaining «electroluminescent» polymers, or further for collecting and transferring solar energy.

In order to obtain fluorescent polymers, there exist several methods. The simplest one consists of dispersing fluorescent molecules in a matrix of the polymer type. Campbell and Bartlett [7] have thereby synthesized monodispersed poly(methylmethacrylate) (PMMA) spheres by copolymerization of methyl methacrylate and of methacrylic acid in the presence of a non-polymerizable dye. Strongly fluorescent PMMA colloids were thus obtained.

Molecular Probes® [21] markets polystyrene microspheres with various sizes and different colors depending on the nature of the dye which is dispersed therein (Fluo-Spheres®). These fluorescent beads have been used as microinjectable cell tracers, as antigen markers, for flow cytometry or further for studying phagocytosis phenomena or measuring blood flow in tissues. Although these microspheres have high gloss and do not seem to undergo any notable photobleaching, the fact that the dye is not covalently attached to the matrix implies an heterophase formation and a risk of salting out the dye into the biological medium. Covalent grafting of the fluorophore is therefore preferable in order to avoid these drawbacks.

Another listed method therefore consists of «post-functionalizing» non-fluorescent polymer chains from substituents allowing reactive coupling with a fluorophore. Saegusa [22] thus described the synthesis of poly-oxazolines by polymerization of 2-methyl-2-oxazoline by ring opening, and then the functionalization of the polymer by hydrolysis of the side methyl group, followed by coupling with 7-coumaryloxyacetic acid.

Also, the document of Rhum and Matthews [23] relates to the copolymerization of hydroxyethyl methacrylate (HEMA) and of methyl methacrylate (MMA), followed by the coupling of the hydroxyl group of HEMA with 4-carboxymethyl-umbelliferone, thereby giving a pH indicator which is not water-soluble.

Similarly, the document of Bouma and Celebuski [24] is related to derivatives of 7-hydroxycoumarin having substituents in position 4. These substituents include functional groups allowing them to be coupled with biological molecules, these are typically substituents with —OH, —SH or —NH₂ end groups.

However, this «post-functionalization» method is only applied to a restricted number of polymers having adequate functional groups such as —COOH, —OH, —SH, —NH₂, or —NCO and does not allow control either of the level or of the distribution of the grafting of the fluorophore on the polymer.

It should be noted that these functional groups are not groups which may be described as polymerizable groups.

The fluorophores which may be used directly as a monomer or comonomer, have the advantage of eliminating the disadvantages mentioned above. Pitschke et al. [25] describe the synthesis of a monomer derived from 7-aminocoumarin, substituted in position 3 with a polymerizable styrenic group (Formula 1a below). However, substitution of the coumarin ring in position 3 is known for deeply changing the electronic properties of the original coumarin ring [23].

Rathbone et al. [26], as for them, describe the use of the 7-hydroxy_4-methylcoumarin acrylate monomer (Formula 1b below) for the synthesis of fluorescent polymers having molecular print. However the blocking of the phenol function in position 7 by the acrylate group causes the loss of an interaction site via a hydrogen bond essential for many applications such as notably pH measurements.

Structure of the fluorescent monomers described by Pitschke et al. (1a) and by Rathbone et al. (1b).

As a summary, the dispersion of dye in polymers is not satisfactory since in this case the dye is not covalently grafted to the polymer, by which it is not possible to ensure sufficient durability and this causes a risk of salting-out of the dye.

Moreover, the reactive coupling of a dye on preformed polymer chains, does not allow control of the grafting (level and distribution) and therefore of the physicochemical properties of the materials on the one hand and restricts both the number of polymers and the type of dye which may be used, to compounds including reactive functions such as —OH, —NH₂, —SH, —NCO, —COOH on the other hand.

Finally, we noticed that only a restricted number of directly polymerizable fluorophores are marketed to this day and the rare coumarin derivatives chemically modified so as to become polymerizable, no longer have the original properties of coumarin.

Therefore, considering the foregoing, there exists a need for a fluorescent compound or fluorophore derived from coumarin and notably from 7-hydroxycoumarin which is directly polymerizable i.e. provided with a polymerizable substituent, but in which the electronic properties and the photoluminescence of the coumarin ring are not or substantially not affected by this polymerizable substituent.

In other words, there exists a need for a polymerizable fluorescent compound derived from coumarin as a basic fluorophore in which the original properties, notably the electronic properties and photoluminescence properties of this basic fluorophore are entirely or at least for a major part preserved.

In particular, it would be interesting to be able to have a polymerizable monomer, compound derived from 7-hydroxycoumarin in which all the properties of 7-hydroxycoumarin would be preserved and in which the phenol function in position 7 of the coumarin ring, the importance of which is known in many applications, would be left intact.

Further, there exists a need for such a polymerizable fluorescent compound which may be easily polymerized, notably by radical polymerization methods either controlled or not, and which may therefore be covalently bound to chains of homopolymers and/or copolymers for example of vinyl, acrylic or styrenic homopolymers and/or copolymers.

The goal of the invention is to provide a polymerizable compound, further called a polymerizable monomer, which inter alia meets the needs listed above.

The goal of the invention is further to provide a polymerizable compound which does not have the drawbacks, defects, limitations and disadvantages of the polymerizable compounds mentioned above and which solves the problems of these compounds.

SUMMARY OF THE INVENTION

This goal and still other ones are achieved according to the invention with a polymerizable fluorescent compound of 7-hydroxycoumarin which is Ethyl-2-methacrylate Umbelliferone-4-acetate.

The compound according to the invention has not been described in the prior art.

The compound according to the invention may be defined as a polymerizable polar fluorescent derivative of 7-hydroxycoumarin which has in position 4, a polymerizable substituent which does not modify or which does not substantially modify the electronic properties and the photoluminescence of the basic coumarin ring.

The compound according to the invention may in particular be considered as a derivative of 4-methylumbelliferone further called 7-hydroxy-4-methylcoumarin.

The compound according to the invention does not have the drawbacks of known fluorophores based on coumarin, described above and provides solutions to the problems posed by these known fluorophores based on coumarin.

Thus, in the compound according to the invention, the electronic properties and photoluminescence properties of the original fluorophore, i.e. 7-hydroxycoumarin are preserved by functionalization of the coumarin ring specifically in position 4 on the one hand, and accessibility of the original phenol function in position 7 is preserved on the other hand.

It is extremely important that this function be preserved in the monomer, compound according to the invention since it is essential for pH measurements and for generating interactions via hydrogen bonds with other substrates or molecules for applications in the field of detection for example.

As a conclusion according to the invention, chemically modified compounds of coumarin are provided for the first time in order to become directly and easily polymerizable and which surprisingly always have the advantageous properties of basic coumarin, such as 7-hydroxycoumarin.

The invention further relates to a method for preparing Ethyl-2-methacrylate Umbelliferone-4-acetate, in which umbelliferone-4-acetic acid is reacted with a compound which is 2-hydroxyethyl methacrylate, comprising a reactive function B which is a hydroxyl function capable of reacting with the carboxylic acid group of umbelliferone-4-acetic acid on the one hand, and a polymerizable chemical group R which is a methacrylate group on the other hand, whereby coupling of the carboxylic acid group of umbelliferone-4-acetic acid with the reactive function B occurs to form Ethyl-2-methacrylate Umbelliferone-4-acetate.

The invention also relates to a fluorescent polymer which is obtainable by polymerization of a polymerizable fluorescent monomer compound of 7-hydroxycoumarin having the following formula (I):

(I)

wherein G is a substituent comprising a polymerizable chemical group R;

and optionally of at least one other polymerizable monomer (IV).

By polymerizable chemical group in the sense of the invention, is meant any group capable of undergoing a polymerization reaction. Polymerization reactions in the sense of the invention include not only polymerization reactions strictly speaking but also inter alia condensation and coupling reactions.

Advantageously, the polymerizable chemical group R is selected from groups comprising an ethylenically unsaturated carbon-carbon double bond; groups allowing condensation reactions; and groups allowing organometallic or oxidant coupling reactions.

Advantageously, the polymerizable chemical group R may be selected from vinylic, styrenic, dienic, acrylic and methacrylic groups.

Among the compounds of formula (I), Ethyl-2-methacrylate Umbelliferone-4-acetate is a novel compound.

The compounds of formula (I) may be defined as polar polymerizable fluorescent derivatives of 7-hydroxycoumarin which have in position 4, a polymerizable substituent which does not modify or which does not substantially modify the electronic properties and photoluminescence of the basic coumarin ring.

The compounds of formula (I) may in particular be considered as derivatives of 4-methylumbelliferone further called 7-hydroxy-4-methylcoumarin.

In the compounds of formula (I) on the one hand, the electronic and photoluminescence properties of the original fluorophore, i.e. 7-hydroxycoumarin, are preserved by functionalization of the coumarin ring specifically in position 4, and on the other hand accessibility of the original phenol function in position 7 is preserved.

It is extremely important that this function be preserved in the compound, monomer of formula (I), since it is essential for pH measurements and for generating interactions via hydrogen bonds with other substrates or molecules for applications in the field of detection for example.

As a conclusion, the compounds of formula (I) are chemically modified coumarin compounds in order to become directly and easily polymerizable, and which, surprisingly, always have all the advantageous properties of the basic coumarin such as 7-hydroxycoumarin.

The compounds of formula (I) may be prepared by a method in which a compound of formula (II):

(II)

wherein H is a substituent comprising a reactive function A, is reacted with a compound (III) comprising a reactive function B which may react with the reactive function A on the one hand and a polymerizable chemical group R on the other hand, by means of which coupling of the reactive function A with the reactive function B occurs in order to form the substituent G comprising the polymerizable chemical group R.

This method may be defined as a method for synthesizing a fluorescent polymerizable monomer belonging to the coumarin family.

More exactly, this method consists of coupling a coumarin (II) for which the substituent of the aromatic ring in position 4 comprises a reactive function A, with a compound, which may also be called a polymerizable monomer itself including a reactive function B capable of reacting with the reactive function A.

The coupling of both compounds, entities (II) and (III) via both compatible functions A and B is achieved without affecting the properties of the original coumarin, notably the emission properties of the original coumarin and leaving the polymerizable group R intact.

Further, in this method, the important —OH function in position 7 of the coumarin ring is not affected by the coupling, while the coumarin is provided in position 4 (away from position 7) with a polymerizable group R which does not affect the fundamental properties of the coumarin ring and which allows easy polymerization of the fluorescent compound.

Advantageously, the reactive function A and the reactive function B may be selected from amine, hydrazine, hydrazone, azide, isocyanate, isothiocyanate, alkoxyamine, aldehyde, epoxy, nitrile, maleimide, halogeno, hydroxyl, thiol, anhydride, carboxylic acid, acid chloride such as acyl chloride, groups.

Of course A and B are generally selected so as to be compatible, i.e. able to react together in order to form a covalent bond.

The reactive function A may be directly connected to the coumarin ring or else it may be connected to the coumarin ring through a spacer arm such as an alkylene group, preferably an alkylene group with 1 to 10 carbon atoms, still preferably from 1 to 4 carbon atoms, which may optionally be interrupted with one or several groups selected from —O—; —CO—; —S—; and —N—.

The whole of the reactive function A and of the spacer arm then forms the substituent H of the compound (II).

Advantageously, the polymerizable chemical group R is selected from groups comprising an ethylenically unsaturated carbon-carbon double bond; groups allowing condensation reactions; and groups allowing organometallic or oxidant coupling reactions.

Advantageously, the polymerizable chemical group R may be selected from vinylic, styrenic, dienic, acrylic and methacrylic groups.

Advantageously, the compound (III) may be selected from alkyl acrylates, alkyl methacrylates, alkyl acrylamides, alkyl methacrylamides, vinyl esters, styrene, and dienes comprising a reactive function B.

In particular one of the reactive function A and the reactive function B may be a carboxylic acid group, and the other one of the reactive function A and of the reactive function B may be a hydroxyl function and the coupling of the reactive function A with the reactive function B may then occur according to an esterification reaction.

Advantageously, the compound (II) may be umbelliferone-4-acetic acid and the compound (III) may be a compound with a reactive function B which is a hydroxyl function such as 2-hydroxyethyl methacrylate and the novel compound Ethyl-2-methacrylate Umbelliferone-4-acetate is thereby prepared.

The fluorescent polymer according to the invention therefore comprises repeating units stemming from the fluorescent monomer compound of formula (I) and optionally repeating units stemming from at least one other polymerizable monomer (IV).

In the same way as the compound of formula (I) the properties of the original coumarin, notably the emission properties of the original coumarin are not affected and are entirely preserved in the polymer according to the invention.

Further, in the polymer according to the invention, the important —OH function in position 7 of the coumarin ring is not affected by the polymerization and remains free, available.

The polymer according to the invention therefore benefits from all the advantageous properties of the monomer of formula (I) from which it is derived.

The polymer according to the invention may be a homopolymer which is obtainable by polymerization of a fluorescent monomer compound of formula (I).

Such a homopolymer has never been described or suggested in the prior art.

Preferably, this homopolymer is obtainable by polymerization of Ethyl-2-methacrylate Umbelliferone-4-acetate.

Or else, the polymer according to the invention may be a random, alternating or sequenced (block) copolymer which is obtainable by polymerization of at least one fluorescent monomer compound of formula (I) and of at least one other copolymerizable monomer.

Advantageously, this other copolymerizable monomer is selected from acrylic monomers, styrenic monomers and vinylic monomers.

Preferred copolymers are the preferably random copolymer which is obtainable by copolymerization of Ethyl-2-methacrylate Umbelliferone-4-acetate, of 2-hydroxyethyl methacrylate, and of divinylbenzene, and the preferably random copolymer which is obtainable by copolymerization of Ethyl-2-methacrylate Umbelliferone-4-acetate, of 4-vinylpyridine, and divinylbenzene.

The polymer according to the invention may advantageously appear in the form of spheres, notably microspheres with a diameter from 0.1 to 500 μm, preferably from 0.1 to 200 μm.

The polymer according to the invention may appear in the form of a thin film deposited on at least one surface of a substrate, or of a thick film.

The invention further relates to a sensor comprising the polymer according to the invention as a sensitive material.

The application of the polymers according to the invention in such sensors has never been described or suggested in the prior art.

Advantageously, this sensor is an optical sensor, the operation of which is based on the measurement of variations in the intensity of the fluorescence emitted by the polymer.

The invention further relates to the use of the sensors as defined above for detecting and/or assaying one or several target compound(s), molecule(s).

Preferably, this(these) compound(s) is(are) in a vapor phase, in a gaseous form.

These compounds to be detected and/or to be assayed may notably be selected from nitrated compounds and organophosphorus compounds.

The nitrated compounds may be selected from nitroaromatic compounds, nitramines, nitrosamines and nitric esters.

Preferably, the fluorescent polymer according to the invention and therefore the sensor comprising this polymer may be used for detecting and/or assaying explosives or toxic, in particular neurotoxic, compounds, notably gases.

The invention finally relates to the use of the polymers according to the invention for making fluorescent probes, for making biological markers, for making fluorescent, photoluminescent, and/or radioluminescent and/or cathodoluminescent materials.

Other features and advantages of the invention will become better apparent upon reading the description which follows, given as an illustration and not as a limitation, and which is made with reference to the appended drawings wherein:

BRIEF DESCRIPTION OF THE DRAWINGS

The fluorescence intensity (in a.u.) is plotted in ordinates, and the wavelength (in nanometers) is plotted in abcissae.

The variation in the fluorescence intensity is plotted in ordinates (in % of the value at t=0), and time (in minutes) is plotted in abscissae.

DETAILED DISCUSSION OF CERTAIN ILLUSTRATIVE EMBODIMENTS

The polymerizable fluorescent compounds or monomers of 7-hydroxycoumarin which may be used for preparing the polymers according to the invention have the following formula (I):

(I)

wherein G is a substituent comprising a polymerizable chemical group R.

R is generally a group comprising an ethylenically unsaturated carbon-carbon double bond.

Other polymerizable chemical groups are groups allowing condensation reactions or groups allowing organometallic or oxidant coupling reactions.

Among the groups R comprising an ethylenically unsaturated carbon-carbon double bond, mention may be made of vinylic, styrenic, dienic, acrylic and methacrylic groups.

The group R may be directly connected to the coumarin ring in position 4 of the latter or else it may be connected to the coumarin ring via a binding group such as an alkylene group, generally comprising from 1 to 10 C atoms, preferably from 1 to 4 C atoms, which may optionally be interrupted by one or several groups selected from —O—; —CO—; —S—; and —N—.

Among these fluorescent compounds, some are novel, in particular Ethyl-2-methacrylate Umbelliferone-4-acetate.

The invention therefore also relates to Ethyl-2-methacrylate Umbelliferone-4-acetate as a novel compound.

The method for preparing the compounds of formula (I) consist of coupling according to Scheme 1, a 7-hydroxycoumarin, the substituent of the aromatic ring of which in position 4 comprises a reactive function A, with a polymerizable monomer comprising a polymerizable group R and a reactive function B, which may react with the reactive function A.

The coupling of these two entities, i.e. 7-hydroxycoumarin on the one hand and the polymerizable monomer on the other hand does not affect the emission properties of the initial 7-hydroxycoumarin.

Scheme 1: Principle for Synthesizing Polymerizable Coumarin Derivatives of Formula (I).

The reactive function A and the reactive function B may be selected from amine, hydrazine, hydrazone, azide, isocyanate, isothiocyanate, alkoxyamine, aldehyde, epoxy, nitrile, maleimide, halogeno, hydroxy, thiol, anhydride, carboxylic acid, acid chloride such as acyl chloride, groups.

In Scheme 2, R represents any type of polymerizable chemical group, as defined above.

Any monomer comprising at least one reactive function B capable of reacting with the reactive function A, and a polymerizable group R other than said reactive function B may be suitable for achieving the synthesis of a polymerizable compound of formula (I) by the method discussed above.

In this polymerizable monomer, the reactive function B and the polymerizable group R may be directly connected but they are generally separated by a binding group such as an alkylene group, generally comprising from 1 to 10 C atoms, preferably from 1 to 4 C atoms, which may optionally be interrupted by one or several groups selected from —O—; —CO; —S—; and —N—.

A particularly suitable monomer, the structure of which is illustrated below (formula (2)) is 2-hydroxyethyl methacrylate which has, as a reactive function B, a reactive alcohol function and as a polymerizable group R, a methacryl group, R and B being connected through a chain —(CO)—O—(CH$_2$)$_2$—OH.

(2)

Other non-limiting examples of suitable monomers for synthesizing the polymerizable fluorescent monomer, compound of formula (I) are functional derivatives of monomers such as alkyl acrylates, alkyl methacrylates, alkyl acrylamides, alkyl methacrylamides, vinyl esters, styrenes and dienes. By functional derivatives is meant that these compounds in addition to a polymerizable group such as a methacryl, acryl, vinyl group, comprise a reactive function B as defined above.

The man skilled in the art will know how to select from functions A and functions B those which may give the adequate coupling reactions and will easily determine the conditions of these reactions, notably so that the hydroxyl group in position 7 is not affected.

In particular, the coupling reaction between the reactive function A and the reactive function B may be an esterification reaction between an alcohol and a carboxylic acid, the carboxylic acid may equally be the reactive function A or the reactive function B.

According to a preferred embodiment of the invention, it is therefore possible to start from umbelliferone-4-acetic acid, which is a derivative of 7-hydroxycoumarin substituted in position 4 with an acetic acid group and which has the following formula (3):

(3)

The preparation of the fluorescent derivative of 7-hydroxycoumarin, substituted in position 4 with a polymerizable group is carried out according to the synthesis scheme 2.

Scheme 2: Synthesis of a Fluorescent Monomer Derived from 7-hydroxycoumarin (R: Group Bearing a Polymerizable Function).

The coupling is accomplished according to an esterification reaction between the compound illustrated in FIG. 4 and an alcohol bearing a polymerizable group R in the presence of dicyclohexylcarbodiimide and of a nitrogen-containing base such as ethylpyridine in a solvent such as THF.

A polymerizable fluorescent monomer derived from 7-hydroxycoumarin which bears a polymerizable function R for example comprising an ethylenically unsaturated carbon-carbon double bond is thereby obtained.

A novel preferred polymerizable fluorescent monomer, compound according to the invention, the synthesis of which may be carried out by the method described above, is Ethyl-2-methacrylate Umbelliferone-4-acetate of formula (4).

(4)

This compound may be prepared by an esterification reaction of the compound of formula (3) with 2-hydroxyethyl methacrylate illustrated by formula (2).

According to the invention, polymers, homopolymers and copolymers may be prepared by polymerization of the polymerizable fluorescent monomers of formula (I) as described above and the synthesis of which has also been described above.

The polymer according to the invention may be a homopolymer, i.e. it is prepared from a single monomer compound of formula (I). In other words, it consists of a single repeating unit derived from a monomer, compound of formula (I).

Such a homopolymer may be prepared by any known polymerization method. However, preferably, this homopolymer is prepared by a radical polymerization method, either controlled or not.

A homopolymer according to the invention generally has a degree of polymerization n from 1 to 10,000, preferably from 5 to 100.

In particular, the invention relates to homopolymers which are obtainable by polymerization of the compound of formula (6) Ethyl-2-methacrylate Umbelliferone-4-acetate.

These homopolymers are illustrated by formula (5):

(5)

wherein n is an integer from 1 to 10,000, preferably from 5 to 100.

It was shown that the homopolymer of formula (5), prepared from Ethyl-2-methacrylate Umbelliferone-4-acetate unexpectedly has singular properties.

Indeed, it was seen that the homopolymer corresponding to a degree of polymerization of n~120, has a temperature transition of the LCST (Lower Critical Solution Temperature) type when it is solubilized in tetrahydrofurane (THF).

Thus, at room temperature, the polymer solution in THF is monophasic. When the solution is heated, a phase separation and a biphasic mixture is observed. The phenomenon is perfectly reversible and a clear, limpid solution is recovered if the sample is left to return to room temperature.

The pendant coumarinyl group may actually form an « intraunit » H bond (Formula 6) or an « interunit/interchain » H bond (Formula 7) which may justify the existence of this transition. This original property may thereby be utilized for making fluorescent thermometers for example.

(6)

(7)

(8)

The copolymer illustrated in this formula (8) where n and n' are as defined above, may be a random copolymer, or an alternating copolymer, or a block copolymer.

Further, the copolymers according to the invention may be water-soluble or else soluble in organic solvents while homopolymers are generally only organosoluble. This solubility of the polymers according to the invention proves to be particularly of interest for preparing thin films from these polymers.

Their solubility notably in water may be easily controlled by the man skilled in the art by adjusting the nature and the proportion of each of the comonomers. Thus, if it is desired that the copolymer be soluble in water, the other polymerizable monomer will be selected from hydrophilic monomers known to the man skilled in the art in a proportion such that the sought solubility is obtained.

The copolymers according to the invention may be prepared by any known polymerization method. However, preferably these copolymers are prepared by a radical polymerization method, either controlled or not. As this was specified above according to the reactivity ratio of the comonomers, the obtained copolymers may be random, alternating or block copolymers and the solubility of the polymers may be controlled by the man skilled in the art by adequately selecting the nature and the proportion of each of the comonomers.

The polymer according to the invention may appear in any form.

The polymer according to the invention may advantageously appear in the form of spheres, notably of microspheres with a diameter of 0.1 to 500 μm, preferably from 0.1 to 200 μm.

The polymers according to the invention may appear in the form of a monolith, for example a cylinder preferably having some porosity so as to make the totality of the polymer accessible to compounds to be detected or to be assayed.

The polymers according to the invention may also appear as films.

These films may be thin films, generally deposited on at least one surface of a substrate. In the case of a planar substrate, this thin film may cover one or both faces of the substrate.

When the polymer according to the invention appears as a thin film, the latter generally has a thickness from 10 angstroms to 100 microns.

Such a film may be prepared by any method known to the man skilled in the art for preparing a thin film on the surface of a substrate for example:

by spraying, spin coating, or drop coating;
by dip-coating;
by the Langmuir-Blodgett technique;
by electrochemical deposition;

Therefore, another interesting innovation related to the synthesis of this type of fluorescent monomer is the possibility of forming an intramolecular hydrogen bond, providing singular properties to the polymers which are derived therefrom.

Alternatively, the polymer according to the invention may be a copolymer, i.e. it is then prepared by polymerization of several monomers according to the invention which all have formula (I), or by polymerization of one or more monomer(s) of formula (I) according to the invention and of one or several other polymerizable monomer(s).

This(these) other copolymerizable monomer(s) may be selected from (meth)acrylic monomer(s), styrenic monomers and vinylic monomers.

Examples of these other copolymerizable monomers are methyl acrylate, methyl methacrylate, cyanoethyl acrylate, 2-hydroxyethyl methacrylate, divinylbenzene, 4-vinylpyridine.

The fluorescent copolymers according to the invention may be random, alternating or sequenced (block) copolymers depending on the reactivity ratios of the comonomers.

Preferred copolymers are the copolymers which are obtainable by copolymerization of Ethyl-2-methacrylate Umbelliferone-4-acetate, 2-hydroxy-ethyl methacrylate, and divinylbenzene, and the copolymers which are obtainable by copolymerization of umbelliferone-4-ethyl acetate-2-methacrylate, of 4-vinyl-pyridine and of divinylbenzene.

In the copolymers according to the invention prepared from a fluorescent monomer of formula (I) according to the invention and from another polymerizable monomer, the degree of polymerization n of the fluorescent monomer of formula (I) according to the invention is generally from 1 to 10,000, preferably from 5 to 100, and the degree of polymerization n' of the other monomer is generally from 1 to 10,000, preferably from 5 to 100.

Formula (8) illustrates as an example a fluorescent copolymer stemming from copolymerization of a polymerizable fluorescent monomer of formula (I) according to the invention i.e. Ethyl-2-methacrylate Umbelliferone-4-acetate and of another polymerizable monomer P.

by in situ polymerization, i.e. directly on the surface of the substrate.

The polymers according to the invention generally have solubility in organic solvents such as acetone, chloroform, THF, DMF, DMSO, NMP, which makes them particularly suitable to be used in methods for preparing thin films in a solution.

The polymer according to the invention may also appear as a thick, generally self-supported, film.

Such a thick film generally has a thickness of 100 μm up to one or several mm (for example, 2, 3, 4, 5 mm) and may be prepared by spraying, in situ polymerization, hand coating, hot pressing, extrusion.

The invention further relates to sensors comprising said polymer in any form whatsoever as a sensitive material.

These sensors for example comprising the polymer in the form of a thin layer or as microspheres may notably be optical sensors, the operation of which is based on measuring the variations in the intensity of the fluorescence emitted by the polymer.

The operating principle of optical sensors based on fluorescence has notably been described by B. Valeur in Molecular Fluorescence: Principles and Applications, 2002, Ed, WILEY VCH, New York. Generally, these sensors comprise a substrate made of glass of optical quality, one of the faces of which is covered with a thin film of the sensitive material. The intensity of the fluorescence emitted by the sensitive material may be measured over the whole emission spectrum of this material. However, it is preferable to conduct measurements of fluorescence intensity at the emission wavelength giving the maximum intensity values for the excitation wavelength itself leading to the best signal/noise ratio for acquiring fluorescence intensities.

Sensors including a polymer as defined earlier, as a sensitive material, have proved to have many advantages, notably:
  a capability of specifically detecting nitrated compounds, and in particular nitroaromatic compounds as well as organophosphorus compounds, with great sensitivity since they are capable of detecting their presence at concentrations of less than 1 ppm (parts per million) and even less than a tenth of a ppm, combined with specificity towards these compounds,
  response rapidity and reproducibility of this response,
  stability of the performances over time and, as a consequence, a very satisfactory lifetime,
  a capability of operating continuously,
  a manufacturing cost compatible with the production of sensors in series, a very small amount of polymer (i.e. in practice a few milligrams) being required for manufacturing a sensor, and
  the possibility of being miniaturized and a consequence, of being easily transportable and able to be manipulated on any type of sites.

These sensors may notably be used for detecting and/or assaying one or several target compound(s), molecule(s).

These target compounds may appear in solid, liquid or gaseous form (vapor) but preferably these compounds are in a vapor phase, in a gaseous form.

In other words in the field of chemical detection, fluorescent polymers according to the invention have proved to be capable of indicating the presence of target molecules in a vapor phase. The detection is based on the measurement of fluorescence variations of the polymer, for example in the form of a film, when it is exposed to vapors of the target molecule.

The quality defined by the sensitivity, the selectivity and the reversibility of the detection is for a major part conditioned by the properties of the sensitive layer and it was found that the fluorescent polymers according to the invention have particularly interesting photoluminescence properties for this type of application with view to detecting and/or assaying compounds.

The compounds to be detected and/or to be assayed may notably be selected from nitrated compounds and organophosphorus compounds.

The nitrated compounds may be selected from nitroaromatic compounds, nitramines, nitrosamines and nitric esters.

As examples of nitroaromatic compounds, mention may be made of nitrobenzene, dinitrobenzene, trinitrobenzene, nitrotoluene, dinitrotoluene, trinitrotoluene, dinitrofluoro-benzene, dinitro-trifluoromethoxybenzene, amino-dinitrotoluene, dinitro-trifluoromethylbenzene, chlorodinitrotrifluoromethyl-benzene, hexanitro-stilbene or further trinitrophenol (or picric acid).

As examples of nitramines, mention may be made of cyclotetramethylenetetranitramine (or octogen), cyclotrimethylenetrinitramine (or hexogen) and trinitrophenylmethylnitramine (or tetryl), while nitrosamines are for example nitrosodimethylamine.

As an example of nitric esters, mention may be made of pentrite, ethylene glycol dinitrate, diethylene glycol dinitrate, nitroglycerin or nitroguanidine.

As examples or organophosphorus compounds, mention may be made of Sarin, VX, Tabun, Soman, Cyclosarin, diisopropyl fluoro-phosphonate (DFP), Amiton or VG, Parathion, dimethoxy methylphosphonate (DMMP).

Preferably, the fluorescent polymer according to the invention and therefore the sensor comprising this polymer may be used for detecting and/or assaying explosives, or toxic, in particular neurotoxic, compounds, notably gases, including organophosphorus pesticides.

As an example, a film of the polymer obtained by copolymerization of the fluorescent monomer Ethyl-2-methacrylate Umbelliferone-4-acetate, 2-hydroxy-ethyl methacrylate and divinylbenzene (see Example 5), unexpectedly has an increase in its fluorescence intensity at 390 nm in the presence of diethyl chlorophosphate vapors (Formula 9), an agent simulating organophosphorus neurotoxic gases. Moreover, a film of a polymer obtained by copolymerization of the fluorescent monomer Ethyl-2-methacrylate Umbelliferone-4-acetate, of 4-vinylpyridine and divinylbenzene, has fluorescence attenuation at 390 nm in the presence of nitrobenzene vapors (Formula 10), an agent simulating nitroaromatic explosives (see Example 5).

Thus, the fluorescence polymers of this invention have fluorescence emission properties which may be utilized for chemical detection.

(9)

(10)

In addition to their use as a sensitive material of sensors, the polymers according to the invention may be used for making fluorescent probes, for making biological markers, for making fluorescent, photoluminescent and/or radioluminescent and/or cathodoluminescent materials. Such materials notably find their application in making imaging devices and fully solid organic lasers.

Thus, in an imaging device, the fluorescent polymer deposited on a substrate, captures photons, electrons, radiations . . . which make it fluorescent. The emitted light is recovered via a CCD camera which allows a space-time analysis to be conducted.

In a solid organic laser, the liquid fluorescent source such as coumarin in solution is replaced with the polymer.

The invention will now be described with reference to the following examples given as an illustration and not as a limitation.

Example 1

Synthesis of the monomer Ethyl-2-methacrylate Umbelliferone-4-acetate (U4AEMA)

$C_{17}H_{16}O_7$
332.31 g/mol
pale yellow crystals
Melting point $P_F$ = 132.2° C.
determined by
(DCS)

In a flask, 1 g (4.5 mmol) of umbelliferone-4-acetic acid and 40 mL of non-stabilized anhydrous tetrahydrofurane are introduced, giving a yellow, clear, limpid solution. Next, 0.48 g (4.5 mmol) of ethylpyridine, 2.96 g (22.5 mmol) of 2-hydroxyethyl methacrylate and 0.94 g (4.5 mmol) of dicyclohexylcarbodiimide dissolved before hand in 35 mL of non-stabilized anhydrous tetrahydrofurane, are added to the solution, away from light. The mixture is stirred at room temperature for 5 hours. After removing the dicyclohexylurea precipitate by filtration, the solvent is evaporated, away from light. The product is purified on a silica gel column eluted with a heptane/acetone (3:1 v/v) mixture. After evaporation of the solvent, the pure product is obtained as a pale yellow solid. After drying, a yield of 68% is obtained.

$^1$H NMR (200 MHz, CDCl$_3$) δ (ppm): 1.91 (3H, t, J=1.5 Hz, —CH$_3$: H$^1$), 3.78 (2H, s, CH$_2$COO, H$^8$), 4.40 (4H, m, O(CH$_2$)$_2$O:H$^{5,6}$), 5.59 (1H, m, =CH$_2$ trans, H$^2$), 6.06 (1H, m, =CH$_2$ cis, H$^2$), 6.24 (1H, s, H$^{10}$), 6.83 (1H, dd, J=2.4/8.6 Hz, H$^{11}$), 6.89 (1H, d, J=2.4 Hz, H$^{13}$), 6.99 (1H, s, OH), 7.46 (1H, d, J=8.6 Hz, H$^{16}$).

$^{13}$C NMR ((200 MHz, CDCl$_3$) δ (ppm): 18.19 (C$^1$), 38.06 (C$^6$), 63.35 (C$^{5,6}$), 103.58 (C$^{13}$), 112.28 (C$^{10}$), 113.53 (C$^{15}$), 125.87 (C$^2$), 126.45 (C$^{16}$), 136.22 (C$^3$), 148.27 (C$^{14}$), 154.83 (C$^9$), 155.62 (C$^{17}$), 160.00 (C$^{11}$), 161.57 (C$^{12}$), 167.51 (C$^4$), 168.69 (C$^7$).

IR (KBr tablet) ν (cm$^{-1}$): 3210 (m), 2959 (f), 1744 (F), 1704 (F), 1686 (F), 1621 (F), 1609 (F), 1566 (F), 1510 (f), 1453 (f), 1403 (m), 1374 (m), 1341 (m), 1321 (F), 1277 (m), 1235 (f), 1208 (f), 1185 (m), 1157 (F), 1141 (m), 1068 (f), 1052 (f), 1035 (1), 962 (f), 950 (f), 935 (f), 894 (f), 876 (f), 843 (f), 821 (f), 744 (f), 717 (f), 698 (f), 653 (f), 610 (f), 593 (f), 484 (f), 455 (f).

Fluorescence (EtOH) $λ_{max}$ (nm): 464 ($λ_x$=370).

Figure 1:
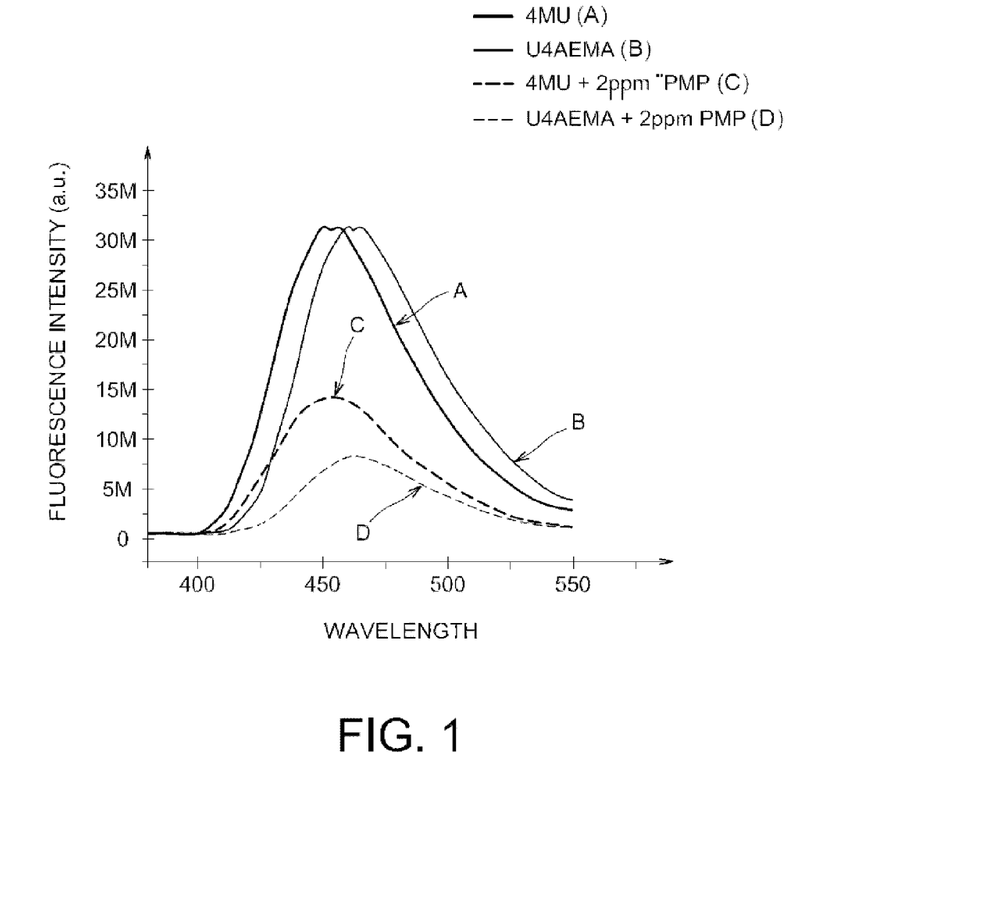
FIG. 1 is a graph which shows the emission spectra of solutions of 4MU (curve A), and of U4AEMA (curve B) at 0.01 g/L in pure ethanol, of a 0.01 g/L 4MU solution in pure ethanol with addition of ppm of PMP (curve C), and of a 0.01 g/L U4AEMA solution in pure ethanol with addition of 2 ppm of PMP (curve D), for an excitation wavelength $\lambda_x$ of 370 nm. The spectra of 4MU and of U4AEMA were normalized to the same intensity.

In order to make sure that the functionalization of the fluorophore is actually without any consequence on its fluorescence properties, we compared the emission spectra of solutions of 4-methylumbelliferone (4MU) and of Ethyl-2-methacrylate Umbelliferone-4-acetate (U4AEMA) in ethanol (0.01 g/L). FIG. 1 shows the results obtained as well as the effect of adding a solution of a phosphonic acid (pinacolyl methylphosphonate or PMP, 2 ppm).

FIG. 1 shows that the functionalization of 4MU is expressed on the emission spectrum by a bathochromic shift of 10 nm thereby showing that its electronic properties have not been modified in a noticeable way. The thereby functionalized fluorophore still remains sensitive to the presence of an acid in the medium and undergoes attenuation of fluorescence at 460 nm.

Example 2

Synthesis of the homopolymer poly(Ethyl-2-methacrylate Umbelliferone-4-acetate) (poly U4AEMA)

Yellow solid Glass
transition temperature,
$T_g$ = 105° C.

In a three-necked flask, 300 mg (0.9 mmol) of U4AEMA and 6 mg (~2% by weight) of azobisisobutyronitrile (AIBN) as an initiator, are dissolved in 12 mL of non-stabilized anhydrous tetrahydrofurane (THF), giving a yellow, clear, limpid solution. The mixture is placed for 5 minutes in an ultrasonic bath away from light. The flask is then surmounted with a cooler and placed in an ice bath while argon bubbling is carried out for 10 minutes in the solution. The reaction mixture is heated to 60° C. for 20 hours with magnetic stirring and slight argon flushing, sweeping.

The polymer formed is precipitated from 200 mL of ether. The precipitate is then filtered and rinsed. The obtained solid is taken up in THF, and then again precipitated from the ether. After filtration and rinsing, the solid is dried until its mass is constant. The polymer is recovered as a fluorescent yellow solid with a yield of 52%.

GPC (PS standards in DMF) $M_w$=107300; $M_w/M_n$=2.8

$^1$H NMR (200 MHz, CDCl$_3$) δ (ppm): 0.84 H$^{1,2}$), 3.81 (2H, H$^8$), 4.17 (4H, H$^{5,6}$), 6.11 (1H, H$^{10}$), 6.81 (2H, H$^{15,16}$), 7.37 (1H, H$^{16}$), 10.54 (1H, OH).

IR (KBr tablet) ν (cm$^{-1}$): 3362 (m), 2944 (m), 2803 (f), 2514 (f), 1720 (F), 1609 (F), 1566 (m), 1515 (f), 1445 (m), 1384

(m), 1317 (m), 1267 (m), 1237 (m), 1148 (F), 1138 (F), 1053 (m), 998 (m), 947 (f), 847 (m), 817 (f), 742 (f), 700 (f), 634 (f), 600 (f), 586 (f).

Fluorescence 435 ($\lambda_x$=375).

(Film on quartz) $\lambda_{max}$ (nm)

Example 3

Synthesis of the copolymer poly(umbelliferone-4-ethyl acetate-2-methacrylate-co-styrene)

In a perfectly dry three-necked flask surmounted with a cooler, 5 mg (15 µmol) of U4AEMA and 20 mg (~2% by weight) of AIBN are dissolved in 20 mL of non-stabilized anhydrous tetrahydrofurane (THF), introduced under argon. Next, 1 g (9.6 mmol) of purified styrene is added under argon. The flask is then placed in an ice bath while argon bubbling is carried out for 20 minutes in the solution. The reaction mixture under an inert atmosphere is heated to 60° C. for 40 hours with magnetic stirring. The polymer formed is precipitated from 200 mL of methanol. The precipitate is then filtered and rinsed. The obtained solid is taken up in THF, and then again precipitated from methanol. After filtration and rinsing, the solid is dried to constant mass. The polymer is recovered as fluorescent white solid with a yield of 2%.

GPC (PS standards in THF) $M_w$=6437; $M_n$=5028; $M_w/M_n$=1.28

IR (KBr tablet) v (cm$^{-1}$): 3433 (f), 3100 (f), 3081 (m), 3060 (m), 3025 (F), 3000 (f), 2922 (F), 2847 (m), 1941 (f), 1869 (f), 1800 (f), 1731 (f), 1600 (m), 1582 (f), 1492 (F) 1455 (F), 1368 (f), 1324 (f), 1260 (f), 1180 (f), 1154 (f), 1066 (m), 1028 (m), 976 (f), 961 (f), 938 (f), 904 (f), 837 (f), 801 (f), 756 (F), 700 (F), 668 (f), 538 (m).

Fluorescence 439 ($\lambda_x$=375).

(Film on quartz) $\lambda_{max}$ (nm)

Example 4

Synthesis by precipitation of fluorescent microspheres by copolymerization of Ethyl-2-methacrylate Umbelliferone-4-acetate, of divinylbenzene and of 2-hydroxyethyl methacrylate In a single-necked flask, an acetonitrile/toluene (3:1 v/v) mixture is introduced. 2-hydroxyethyl methacrylate and divinylbenzene are then introduced in a molar ratio of 1:5 respectively and so that the mixture of solvents represents a volume percent of 96.5%. The fluorescent monomer is added in an amount of 1 mol % relative to the other monomers. Once the initiator (AIBN, 2% by weight) is added, the synthesis mixture is placed for 5 minutes in an ultrasonic bath. Argon bubbling for 10 minutes followed by flushing, sweeping for 5 minutes is performed while the mixture is maintained in an ice bath. The flask is then attached onto a rotary arm allowing rotation of the flask around an axis at about 45° C., while immersing it in an oil bath. A temperature ramp is then applied so as to bring the temperature of the oil bath from 20 to 60° C. within 2 hours. The reaction medium is then heated to 60° C. for 18 hours with rotation of the flask at 10 rpm.

The spherical particles formed are recovered either by filtration in vacuo on a Millipore membrane of 0.45 µm, or by centrifugation at 11,000 rpm for 10 minutes (centrifuge Sigma 6K15, Fischer Bioblock Scientific).

The extraction of the monomers having not reacted is performed by Soxhlet extraction with a methanol/acetic acid mixture (9:1, v/v) for one night (with emptying of the extractor about every 20 minutes). Then the materials are rinsed with methanol until a neutral pH is attained. A last washing with acetone is carried out, before drying for one night at 40° C. under a dynamic vacuum.

A white powder is finally obtained (yield 25%) consisting of particles with a diameter of 2 µm.

Example 5

Fluorescent microspheres are synthesized according to the procedure described in Example 4, simply by replacing 2-hydroxyethyl methacrylate with 4-vinylpyridine.

Figure 2:
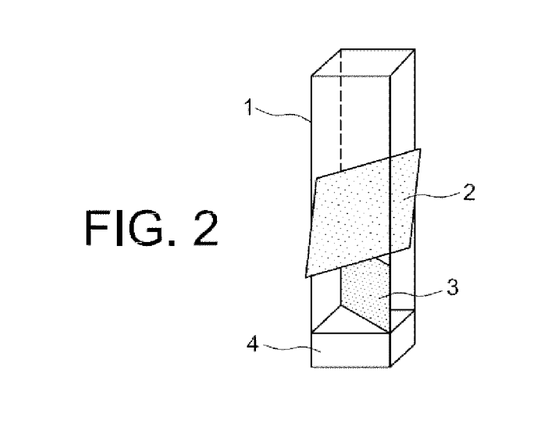
FIG. 2 is a perspective view of a quartz cell for fluorescence measurement mounted for a measurement in a static atmosphere at the saturation vapor pressure of nitrobenzene.

A deposit of these fluorescent microspheres is achieved on a double-sided adhesive which is placed on a quartz substrate (2) before being introduced into a quartz cell for fluorescence (1) containing liquid nitrobenzene (4), as schematized in FIG. 2. The quartz substrate (2) is supported by a sample holder (3). The closed cell is thus at the saturating vapor pressure of nitrobenzene (180 ppm).

Figure 3:
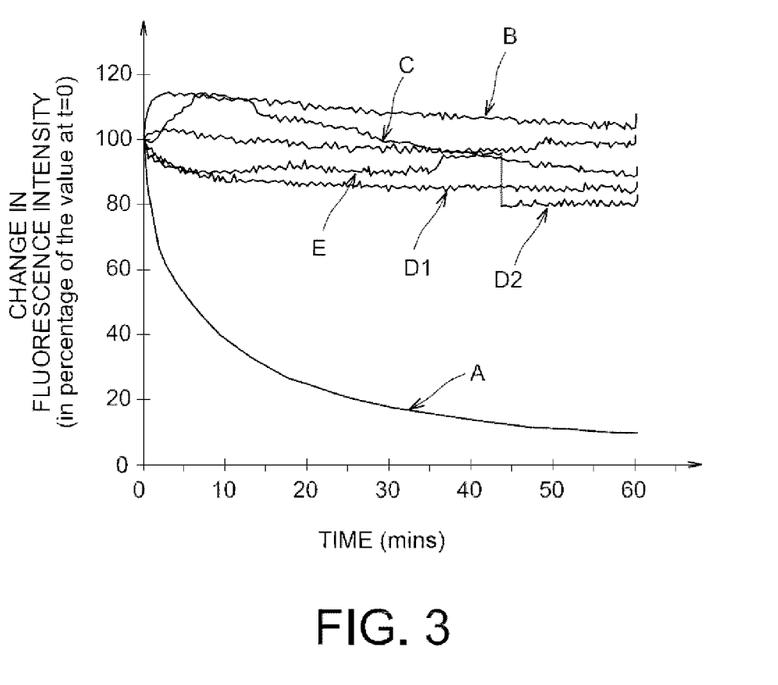
FIG. 3 is a graph which gives the variation in the fluorescence intensity of deposits of a fluorescent copolymer based on Ethyl-2-methacrylate Umbelliferone-4-acetate, on 4-vinylpyridine and on divinylbenzene, in the presence of static vapors of nitrobenzene (Curve A), of ethanol (Curve B), of toluene (Curve C), of acetone (Curves D1 and D2), and of Methyl-Ethyl-Ketone (MEK) (Curve E) (excitation wavelength $\lambda_x$=320 nm, emission wavelength $\lambda_M$=390 nm, slits=0.1 nm, frequency=10 s$^{-1}$).

FIG. 3 illustrates the change in the fluorescence intensity of the microspheres over time, measured at 390 nm for an excitation wavelength of 320 nm, and this as soon as the sample is introduced into the cell. The same experiment is then carried out with fluorescent microspheres in the presence of static vapors of various volatile solvents, i.e. ethanol, toluene, acetone and methylethylcetone. It is thus seen that after one hour, the fluorescence of the polymer is almost completely extinguished in the presence of static vapors of nitrobenzene, while fluorescence only varies by ±10% in the presence of vapors of usual organic solvents, the saturating vapor pressures of which are however much higher. Further, the fluorescence attenuation by nitrobenzene vapors is very fast. The signal drops instantaneously when the deposit is introduced into the cell and 50% of the initial fluorescence are extinguished within 5 minutes. The described fluorescent microspheres are thus capable of indicating the presence of vapors of the nitroaromatic compound and of being used for applications in chemical detection.

REFERENCES

[1] Monfort-Windels, F., Lumière et matière: des interactions au service de la lutte contre la contre-façon. L'Actualité Chimique 2007, 308-309, 108-110.

[2] Théry, E., La trace mise en lumière dans l'enquête policière. L'Actualité Chimique 2007, 308-309, 111-112.

[3] Obert, E.; LeBarny, P. Polymère fluorescent pour capteur physico-chimique. FR-A1-2900408, 2006.

[4] Jenkins, A. L.; Uly, O. M.; Murray, G. M., Polymer-based lanthanide luminescent sensor for detection of the hydrolysis product of the nerve agent Soman in water. Anal. Chem. 1999, 71, 373-378.

[5] Jenkins, A. L.; Yin, R.; Jensen, J. L., Molecularly imprinted polymer sensors for pesticide and insecticide detection in water. Analyst 2001, 126, 798-802.

[6] Hairault, L.; Pasquinet, E.; Montméat, P.; Moreau, J.; Lère-Porte, J.-P.; Wakim, S.; Serein-Spirau, F. Chemical sensors comprising fluorescent conjugated polymers as sensitive materials, and the use of thereof for the detection or dosage of nitrated compounds. WO-A-2005103653 Application 2005.

[7] Campbell, A. I.; Bartlett, P., Fluorescent Hard-Sphere Polymer Colloids for Confocal Microscopy. Journal of Colloid and Interface Science 2002, 256, 325-330.

[8] Charreyre, M.-T.; Mandrand, B.; Martinho, J. M. G.; Relogio, P.; Sequeira, F. J. P. Polymères fluorescents en solution aqueuse et procédéde préparation de polymères fluorescents solubles en solution aqueuse. FR-A1-2887892, 2005.

[9] Waters, J., F. Aqueous dispersion of fluorescent pigments. WO-A-1996/031565 Application 1996.

[10] Uchiyama, S.; Matsumura, Y.; Silva, A. P. d.; Iwai, K., Fluorescent molecular thermometers based on polymers showing temperature-induced phase transitions and labeled with polarity-responsive benzofurazans. *Analytical Chemistry* 2003, 75, 5926-5935.

[11] Trenor, S. R.; Schultz, A. R.; Love, B. J.; Long, T. E., Coumarins in polymers: From light harvesting to photo-cross-linkable tissue scaffolds. *Chemical Reviews* 2004, 104, (3059-3077).

[12] Bardez, E.; Boutin, P.; Valeur, B., Photoinduced biprotonic transfer in 4-methylumbelliferone. *Chemical Physics Letters* 1992, 191, 142-148.

[13] Cohen, B.; Ruppert, D., Excited state proton-transfer reactions of coumarin 4 in protic solvents. *Journal of Physical Chemistry A* 2001, 105, 7157-7164.

[14] Schulman, S. G.; Rosenberg, L. S., Tautomerization kinetics of 7-hydroxy-4-methylcoumarin in the lowest excited singlet state. *Journal of Physical Chemistry* 1979, 83, 447-451.

[15] Abdel-Mottaleb, M. S. A.; El-Sayed, B. A.; Abo-Aly, M. M.; El-Kady, M. Y., Fluorescence properties and excited state interactions of 7-hydroxy-4-methylcoumarin laser dye. *Journal of Photochemistry and Photobiology, A: Chemistry* 1989, 46, 379-390.

[16] Kudo, D.; Kon, A.; Yoshihara, S.; Kakizaki, I.; Sasaki, M.; Endo, M.; Takagaki, K., Effect of a hyaluronan synthase suppressor, 4-methylumbelliferone, on B16F-10 melanoma cell adhesion and locomotion. *Biochemical and Biophysical Research Communications* 2004, 321, 783-787.

[17] Nakamura, R.; Kuwabara, H.; Yoneda, M.; Yoshihara, S.; Ishikawa, T.; Miura, T.; Nozaka, H.; Nanashima, N.; Sato, T.; Nakamura, T., Suppression of matrix metalloproteinase-9 by 4-methylumbelliferone. *Cell Biology International* 2007, 31, 1022-1026.

[18] Yoshihara, S.; Kon, A.; Kudo, D.; Nakazawa, H.; Kakizaki, I.; Sasaki, M.; Endo, M.; Takagaki, K., A hyaluronan synthase suppressor, 4-methylumbelliferone, inhibits liver metastasis of melanoma cells. *FEBS Letters* 2005, 579, 2722-2726.

[19] Donglei Yu, M. S. L. X. S. L. M.-N. K.-H. L., Recent progress in the development of coumarin derivatives as potent anti-HIV agents. *Medicinal Research Reviews* 2003, 23, (3), 322-345.

[20] Pal, R.; Jr., W. A. P.; Ben-Yashar, V.; Wagner, R. R.; Barenholz, Y., Characterization of the fluorophore 4-heptadecyl-7-hydroxycoumarin: a —S—; —N— probe for the head-group region of lipid bilayers and biological membranes. *Biochemistry* 1985, 24 (3), 573-581.

[21] MolecularProbes. FluoSpheres and TransFluoSpheres Microspheres for Tracing.

[22] Chujo, Y.; Sada, K.; Saegusa, T., Polyoxazoline having a coumarin moiety as a pendant group. Synthesis and photogelation. *Macromolecules* 1990, 23, (10), 2693-2697.

[23] Rhum, D.; Matthews, R. S. Fluorescent polymers. U.S. Pat. No. 5,019,350, 1991.

[24] Bouma, S. R.; Celebuski, J. E. 7-Hydroxy coumarins having substitutions in the 4 position. U.S. Pat. No. 5,208, 350, 1993.

[25] Pitschke, M.; Fels, A.; Schmidt, B.; Heiliger, L.; Kuckert, E.; Riesner, D., Polymeric fluorescent dyes for labeling of proteins and nucleic acids. *Colloid and Polymer Science* 1995, 273, 740-752.

[26] Rathbone, D. L.; Su, D.; Wang, Y.; Billington, D. C., Molecular recognition by fluorescent imprinted polymers. *Tetrahedron Letters* 2000, 41, 123-126.

The invention claimed is:

1. A polymerizable fluorescent compound of 7-hydroxycoumarin which is Ethyl-2-methacrylate Umbelliferone-4-acetate.

2. A method for preparing the compound according to claim 1, comprising:
reacting umbelliferone-4-acetic acid with a compound, which is 2-hydroxyethyl methacrylate, comprising a reactive function B which is a hydroxyl function capable of reacting with a carboxylic acid group of umbelliferone-4-acetic acid on the one hand, and a polymerizable chemical group R which is a methacrylate group on the other hand, whereby coupling of the carboxylic acid group of umbelliferone-4-acetic acid with the reactive function B occurs to form Ethyl-2-methacrylate Umbelliferone-4-acetate.

3. A polymer which is obtainable by polymerization of a polymerizable fluorescent monomer compound of 7-hydroxycoumarin and optionally one other copolymerizable monomer
wherein the polymerizable fluorescent monomer compound of 7-hydroxycoumarin is Ethyl-2-methacrylate Umbelliferone-4-acetate.

4. The polymer according to claim 3, which is a homopolymer obtainable by polymerization of Ethyl-2-methacrylate Umbelliferone-4-acetate.

5. The polymer according to claim 3, wherein the other copolymerizable monomer is selected from the group consisting of acrylic monomers, styrenic monomers and vinylic monomers.

6. The polymer according to claim 5, which is a copolymer obtainable by copolymerization of Ethyl-2-methacrylate Umbelliferone-4-acetate, 2-hydroxyethyl methacrylate, and divinylbenzene, or a-copolymer obtainable by copolymerization of Ethyl-2-methacrylate Umbelliferone-4-acetate, 4-vinyl pyridine, and divinylbenzene.

7. The polymer according to claim 3, which appears in the form of spheres.

8. The polymer according to claim 3, which appears in the form of a thin film deposited on at least one surface of a substrate, or of a thick film.

9. A sensor comprising the polymer according to claim 3 as a sensitive material.

10. The sensor according to claim 9, which is an optical sensor, the operation of which is based on measurement of a variation of an intensity of fluorescence emitted by the polymer.

11. A method of detecting and/or assaying one or several target compound(s) and/or molecule(s) comprising:
measuring a variation of an intensity of fluorescence emitted by the polymer in the sensor of claim 9 when the sensor is exposed to said one or several target compound(s) and/or molecule(s).

12. The method according to claim 11 wherein said target compound(s) is(are) in the vapor phase, in a gaseous form.

13. The method according to claim 11 wherein the target compound(s) is(are) selected from the group consisting of nitrated compounds and organophosphorus compounds.

14. The method according to claim 11, wherein the method is for detecting and/or assaying explosives or toxic, compounds.

15. A method of making fluorescent probes, for making biological markers, for making fluorescent, photoluminescent, and/or radioluminescent and/or cathodoluminescent materials, comprising:

providing the polymer of claim 3 as an optical sensor.

16. The polymer according to claim 6, wherein said copolymer is a random copolymer.

17. The polymer according to claim 7, wherein said spheres are microspheres with a diameter from 0.1 to 500 μm.

18. The polymer according to claim 7, wherein said spheres are microspheres with a diameter from 0.1 to 200 μm.

19. The method according to claim 14, wherein the method is for detecting and/or assaying neurotoxic compounds.

* * * * *